(12) United States Patent
Hart et al.

(10) Patent No.: US 7,112,185 B2
(45) Date of Patent: Sep. 26, 2006

(54) ANTI-INVERSION TROCAR SEAL (75) Inventors: Charles C. Hart, Summerville, SC (US); Henry Kahle, Trabuco Canyon, CA (US); Scott V. Taylor, Mission Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 49 days.

(21) Appl. No.: 10/948,383

(22) Filed: Sep. 23, 2004

(65) Prior Publication Data

US 2005/0065475 A1 Mar. 24, 2005

Related U.S. Application Data (60) Provisional application No. 60/505,791, filed on Sep. 24, 2003.

(51) Int. Cl.
*A61M 31/00* (2006.01)

(52) U.S. Cl. ..................... 604/93.01; 604/256

(58) Field of Classification Search .............. 604/34, 604/164.01, 164.04, 158, 163, 167.06, 93.01, 604/256, 167.01, 264, 167.03, 167.04, 167
See application file for complete search history.

(56) References Cited

U.S. PATENT DOCUMENTS

| | | |
|---|---|---|
| 4,240,411 A | 12/1980 | Hosono |
| 4,653,477 A | 3/1987 | Akui et al. |
| 4,929,235 A | 5/1990 | Merry et al. |
| 5,092,857 A | 3/1992 | Fleischhacker |
| 5,330,437 A | 7/1994 | Durman |
| 5,342,315 A | 8/1994 | Rowe et al. |
| 5,342,316 A | 8/1994 | Wallace |
| 5,385,553 A | 1/1995 | Hart et al. |
| 5,401,248 A | 3/1995 | Bencini |

(Continued)

*Primary Examiner*—Nicholas D. Lucchesi
*Assistant Examiner*—Laura A. Bouchelle
(74) *Attorney, Agent, or Firm*—Kenneth K. Vu; Patrick Y. Ikehana (57) ABSTRACT

The invention is directed to a trocar seal adapted to form a seal around a surgical instrument, the trocar seal comprising a housing having an axis extending between a proximal end and a distal end and forming a working channel sized and configured to receive the surgical instrument; an elastomeric septum seal having a proximal face and a distal face, the septum seal being disposed in the housing and extending transverse to the axis of the housing across the working channel; portions of the septum seal defining a hole having a diameter less than or equal to the diameter of the surgical instrument so that during insertion of the instrument along the working channel the septum seal forms a seal with the instrument; and at least one structure formed integrally with or proximate to the septum seal to prevent inversion of the septum seal upon withdrawal of the surgical instrument. The septum seal or the housing may further comprise a sidewall to include the structure extending from the sidewall to the distal face of the seal to tether the seal distally. The structure may be integrally formed with the proximal face of the septum seal to reinforce the seal, or the structure may be integrally formed with the distal face of the septum seal to tether the seal distally. The structure may be an annular reinforcement or rib, and is formed so as to allow side-to-side movement or floatation of the seal. The trocar seal may further comprise a plurality of radially extending ribs formed on the proximal or distal face of the septum seal to reinforce the seal. The trocar seal may further comprise a tensile element formed on the distal face of the septum seal.

30 Claims, 5 Drawing Sheets

U.S. PATENT DOCUMENTS

| | | |
|---|---|---|
| 5,407,433 A | 4/1995 | Loomas |
| 5,443,452 A | 8/1995 | Hart et al. |
| 5,456,284 A | 10/1995 | Ryan et al. |
| 5,584,850 A | 12/1996 | Hart et al. |
| 5,626,598 A | 5/1997 | Roth |
| 5,628,732 A | 5/1997 | Antoon, Jr. et al. |
| 5,709,664 A | 1/1998 | Vandenbroek et al. |
| 5,752,938 A | 5/1998 | Flatland et al. |
| 5,827,228 A | 10/1998 | Rowe |
| 5,843,046 A | 12/1998 | Motisi et al. |
| 5,895,377 A | 4/1999 | Smith et al. |
| 5,906,595 A | 5/1999 | Powell et al. |
| 5,989,224 A | 11/1999 | Exline et al. |
| 6,093,176 A | 7/2000 | Dennis |
| 6,123,689 A * | 9/2000 | To et al. .................. 604/256 |

* cited by examiner

ANTI-INVERSION TROCAR SEAL

This is a non-provisional application claiming the priority of provisional application Ser. No. 60/505,791, filed on Sep. 24, 2003, entitled "Trocar Seal With Anti-Inversion Properties", which is fully incorporated herein by reference.

BACKGROUND OF THE INVENTION

1. Field of the Invention

This invention relates generally to instrument seals in surgical devices and most specifically to septum seals in laparoscopic trocars.

2. Discussion of Related Art

Less invasive abdominal surgery, commonly referred to as laparoscopic surgery, is undertaken with instruments extending across the abdominal wall. In this procedure, the volume of the abdominal surgical site is increased by inflating the abdomen with a gas. In order to maintain the pressure of the gas within the abdomen while passing instruments across the abdominal wall, access devices, commonly referred to as trocars, are positioned through holes in the abdomen. These trocars are provided with seals which engage the instruments as they are passed through the trocar and into the inflated abdomen.

The seals most commonly used for this purpose are septum seals which are elastomeric and are generally planar in configuration. The septum seals are generally made of a thin material that may tend to engage the body or shaft of an inserted instrument and be drawn along with the axial motion of the instrument as the instrument is placed, used, or removed through the septum seals. These seals extend across a working channel of the trocar and form a seal with the instrument as the instrument is passed through a hole in the septum seal. When the instrument is inserted, the septum seal is pushed generally in the distal direction as it forms a seal with the instrument. When the instrument is withdrawn, the opposite effect occurs; the septum seal is pulled generally in the proximal direction causing the seal to invert. This inversion can add undesirable friction during use of the instrument and may cause the septum to bind or gather between the instrument and portions of the seal housing or floating ring or other adjacent structures when the instrument is withdrawn.

SUMMARY OF THE INVENTION

The invention is directed to a trocar seal adapted to form a seal around a surgical instrument, the trocar seal comprising a housing having an axis extending between a proximal end and a distal end and forming a working channel sized and configured to receive the surgical instrument; an elastomeric septum seal having a proximal face and a distal face, the septum seal being disposed in the housing and extending transverse to the axis of the housing across the working channel; portions of the septum seal defining a hole having a diameter less than or equal to the diameter of the surgical instrument so that during insertion of the instrument along the working channel the septum seal forms a seal with the instrument; and at least one structure formed integrally with or proximate to the septum seal to prevent inversion of the septum seal upon withdrawal of the surgical instrument. In one aspect, the septum seal may further comprise a sidewall including the structure extending from the sidewall to the distal face of the seal to tether the seal distally. In another aspect, the housing may comprise a sidewall including the structure extending from the sidewall to the distal face of the seal to tether the seal distally. In yet another aspect, the structure may be integrally formed with the proximal face of the seal to reinforce the seal, or the structure may be integrally formed with the distal face of the septum seal to tether the seal distally.

The structure may be an annular reinforcement or annular rib, and is formed so as not to prevent side-to-side movement or floatation of the seal. The trocar seal may further comprise a plurality of radially extending ribs formed on the proximal or distal face of the septum seal to reinforce the seal. The trocar seal may further comprise a tensile element formed on the distal face of the septum seal. The tensile element may be formed from surgical suture, an elastomer, a thermoplastic, or a metal wire. It is appreciated that in all of the above aspects of the invention, the structure may include any structure disposed distally of the septum seal and is placed in tension when the seal is moved proximally. Similarly, the structure may include any structure disposed proximally of the septum seal and is placed in compression when the seal is moved proximally.

In another aspect of the invention, a trocar adapted to form a seal around a surgical instrument is disclosed, the trocar comprising a cannula having an axis extending between a proximal end and a distal end; a housing disposed at the proximal end of the cannula and forming with the cannula a working channel sized and configured to receive the surgical instrument; an elastomeric septum seal having a proximal face and a distal face, the septum seal being disposed in the housing and extending transverse to the axis of the cannula across the working channel; portions of the septum seal defining a hole having a diameter less than or equal to the diameter of the surgical instrument so that during insertion of the instrument along the working channel the septum seal forms a seal with the instrument; and at least one structure formed integrally with or proximate to the septum seal to prevent inversion of the septum seal upon withdrawal of the surgical instrument.

These and other features of the invention will become more apparent with a discussion of the various embodiments in reference to the associated drawings.

DESCRIPTION OF THE DRAWINGS

The accompanying drawings, which are included in and constitute a part of this specification, illustrate the embodiments of the invention and, together with the description, explain the features and principles of the invention. In the drawings.

DESCRIPTION OF THE INVENTION

A feature of the present invention is to prevent the septum portion of a trocar seal from inverting during withdrawal of instruments such as laparoscopic clip appliers or laparoscopic graspers. The septum seal normally includes an access hole which is smaller than the diameter of the utilized instrument to affect a seal around the instrument shaft and prevent loss of pneumoperitoneum during laparoscopic procedures. Frictional forces between the instrument shaft and the opening of the septum seal are therefore present and predispose the septum seal to invert during withdrawal of laparoscopic instruments.

Inversion of the septum seal during instrument withdrawal can result in binding of the instrument between the proximal opening of the seal housing, the septum seal, and the shaft of the instrument. This occurs as a result of the septum seal first being pulled into the proximal opening of the seal housing and then being compressed between the instrument shaft and the proximal opening of the seal housing. The present invention includes features which inhibit or prevent inversion of the septum seal during withdrawal of laparoscopic instruments and therefore the present invention eliminates the risk of an instrument binding within the trocar seal during withdrawal.

Another feature of the present invention is that by preventing the inversion of the septum seal, the surface area of the septum which is in contact with the outer diameter of the instrument shaft is limited to the circumference of the opening of the septum seal multiplied by the thickness of the septum seal at the opening. This translates into a reduction of frictional forces between the septum seal and the utilized instrument, which is highly desirable during laparoscopic procedures. If the septum seal is allowed to invert, then the surface area of the septum which is in contact with the instrument is significantly increased, as compared to the present invention, resulting in very high frictional forces which can lead to operative complications at a critical point when the laparoscopic surgeon must quickly and smoothly remove and replace instruments through the trocar. By reducing the frictional forces or instrument drag, the present invention facilitates rapid and smooth instrument exchanges during laparoscopic procedures.

The present invention also facilitates smooth and accurate positioning of instruments such as laparoscopic clip appliers within the peritoneal cavity due to the fact that inversion of the septum seal is prevented. In prior art devices in which the septum seal can invert, axial movement of clip appliers can result in a stutter-step motion which occurs as the septum seal toggles between a non-inverted state and an inverted state. This in turn can cause many difficulties, for example, in positioning of the clip applier jaws over a vessel, delaying placement of the clip or even in misplacing of the clip itself. By eliminating the inversion of the septum seal during instrument positioning within the peritoneal cavity, the present invention facilitates rapid, smooth, and accurate positioning of laparoscopic instruments at the operative site.

The present invention includes novel features which can inhibit the inversion of the septum seal. These features serve generally to either tether the septum seal on its distal side or reinforce the septum seal on its proximal side.

Figure 1:
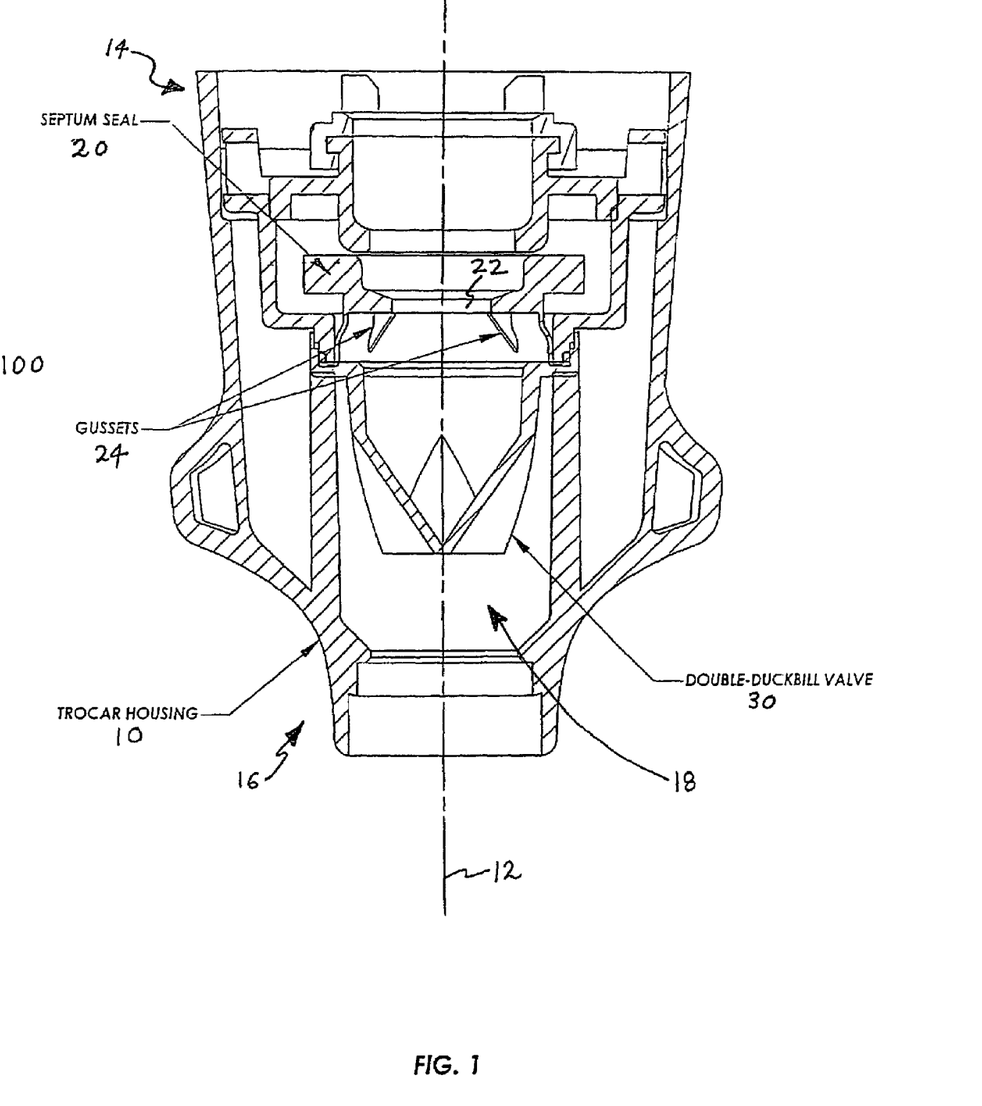
FIG. 1 illustrates an axial cross-section view of a trocar seal including a septum seal and a plurality of gussets in accordance to a first embodiment of the invention.

Referring to FIG. 1, there is shown an axial cross-section view of a trocar seal 100 adapted to form a seal around a surgical instrument. The trocar seal comprises a housing 10 having an axis 12 extending between a proximal end 14 and a distal end 16 and forming a working channel 18 sized and configured to receive the surgical instrument, and an elastomeric septum seal 20 having a proximal face and a distal face, the septum seal 20 being disposed in the housing 10 and extending transverse to the axis 12 of the housing across the working channel 18. It is appreciated that portions of the septum seal 20 define a hole 22 having a diameter less than or equal to the diameter of the surgical instrument so that during insertion of the instrument along the working channel 18 the septum seal forms a seal with the instrument. In this aspect, the seal 20 further includes a plurality of gussets 24 incorporated onto the distal face of the seal 20 to prevent inversion as the surgical instrument is withdrawn from the trocar seal 100. It is appreciated that the trocar seal 100 typically includes a zero closure valve 30 such a double-duckbill valve. Both of the septum seal 20 and the zero closure valve 30 function to form seals across the working channel 18, the septum seal 20 forms its seal in the presence of the surgical instrument while the zero closure valve 30 forms its seal in the absence of the instrument.

In one aspect, the septum seal 20 may further comprise a sidewall including the gussets 24 extending from the sidewall to the distal face of the septum seal 20 and serving to tether the seal distally and thus preventing inversion. The gussets 24 are configured such that side-to-side movement or floatation of the septum seal 20 is not compromised. The gussets 24 may or may not be integral to the septum seal 20. Alternatively, the gussets 24 may be incorporated onto the proximal face of the septum seal 20.

Figure 2:
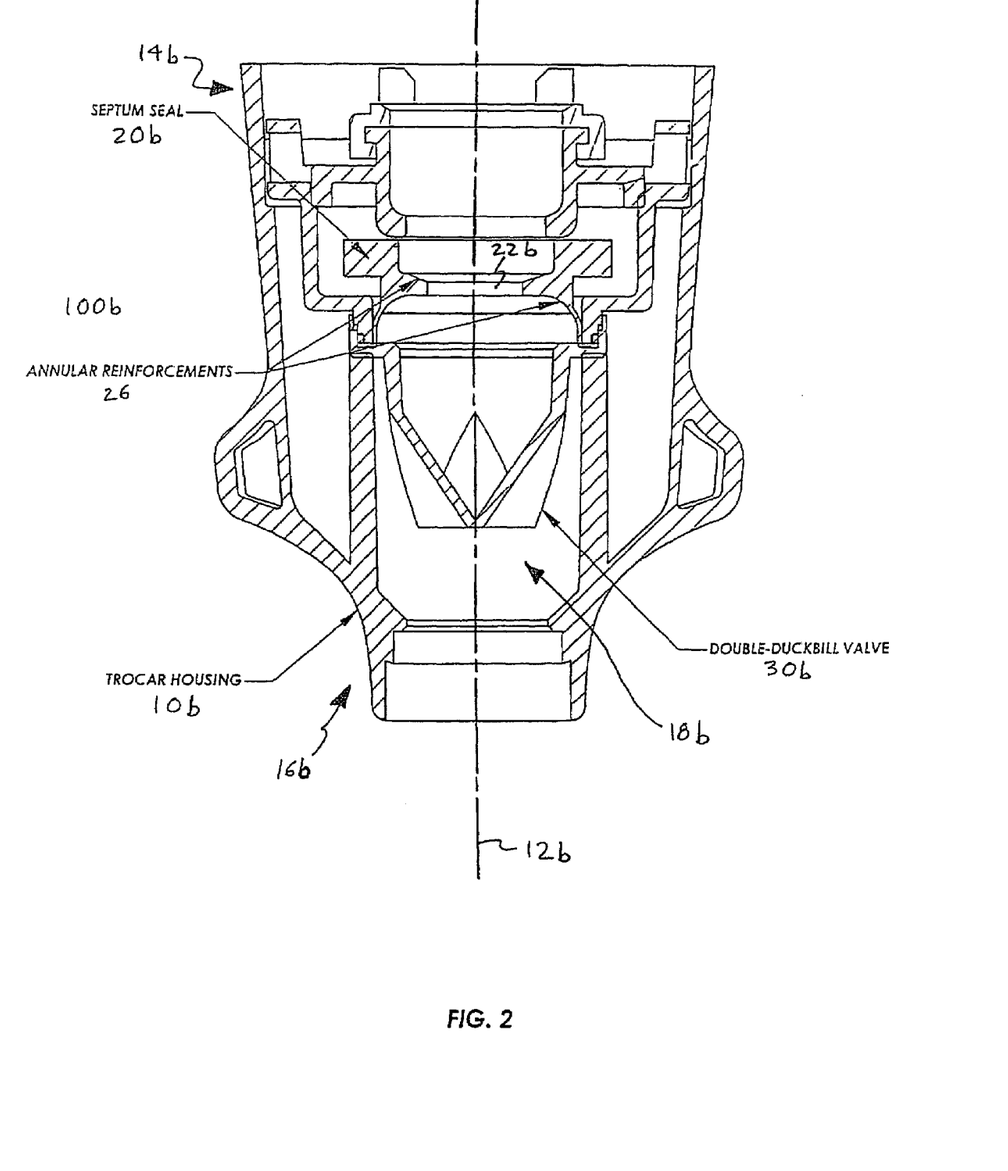
FIG. 2 illustrates an axial cross-section view of a trocar seal including a septum seal and a plurality of annular reinforcements in accordance to a second embodiment of the invention.

Referring to FIG. 2, there is shown an axial cross-section view of a trocar seal 100b, wherein elements of structures similar to those previously discussed are designated by the same reference numeral followed by the lower case letter "b", the trocar seal 100b being adapted to form a seal around a surgical instrument. The trocar seal 100b comprises a housing 10b having an axis 12b extending between a proximal end 14b and a distal end 16b and forming a working channel 18b sized and configured to receive the surgical instrument, and an elastomeric septum seal 20b having a proximal face and a distal face, the septum seal 20b being disposed in the housing 10b and extending transverse to the axis 12b of the housing across the working channel 18b. It is appreciated that portions of the septum seal 20b define a hole 22b having a diameter less than or equal to the diameter of the surgical instrument so that during insertion of the instrument along the working channel 18b the septum seal forms a seal with the instrument. In this aspect, the seal 20b further includes an annular reinforcement 26 incorporated onto the distal face of the seal 20b to prevent inversion as the surgical instrument is withdrawn from the trocar seal 100b. In particular, the annular reinforcement 26 serves to tether the distal face of the septum seal 20b downward and thus prevents inversion. The annular reinforcement 26 is configured so that side-to-side movement or floatation of the septum seal 20b is not compromised. The annular reinforcement 26 may or may not be integral to the septum seal 20b. Alternatively, the annular reinforcement 26 may be incorporated onto the proximal face of the septum seal 20b.

Figure 3:
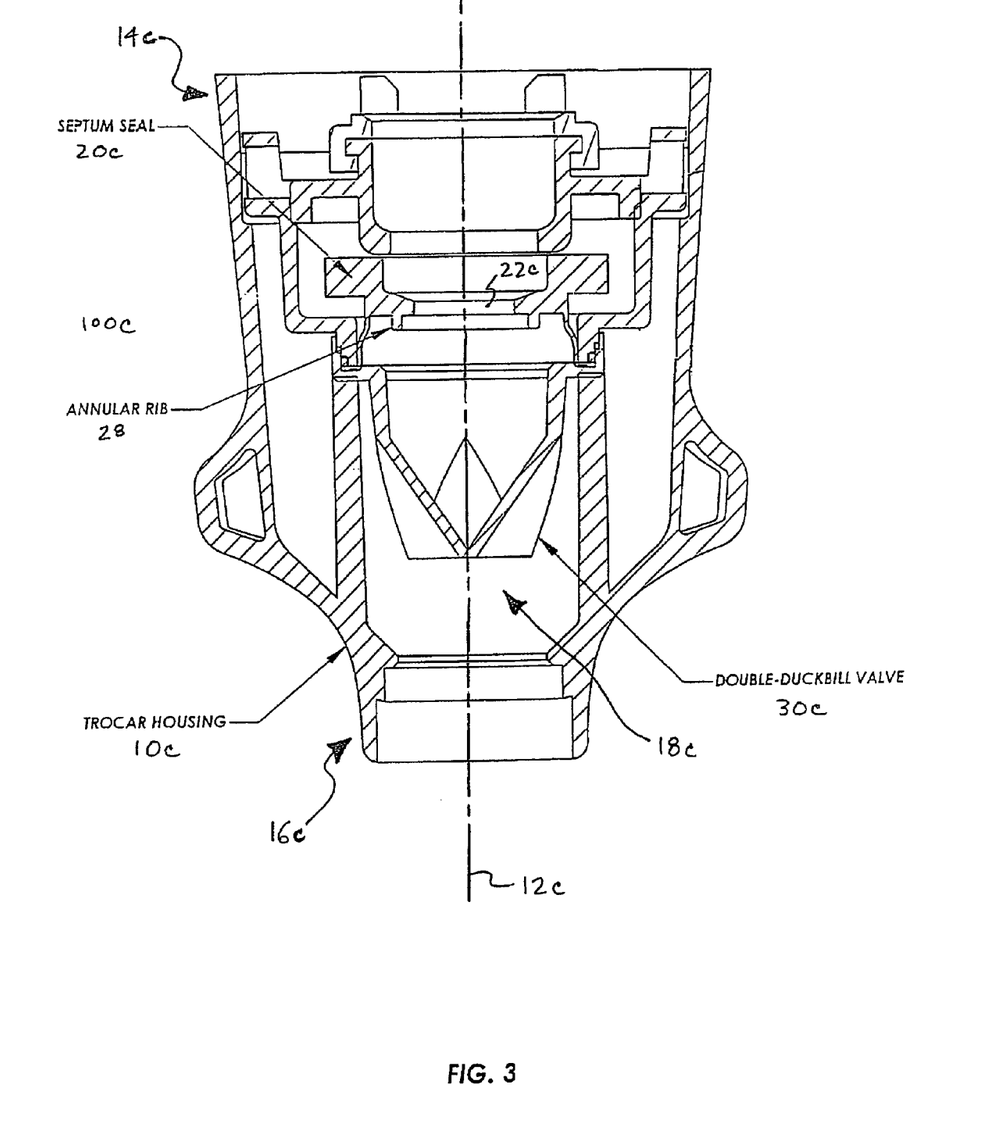
FIG. 3 illustrates an axial cross-section view of a trocar seal including a septum seal and an annular rib in accordance to a third embodiment of the invention.

Referring to FIG. 3, there is shown an axial cross-section view of a trocar seal 100c, wherein elements of structures similar to those previously discussed are designated by the same reference numeral followed by the lower case letter "c", the trocar seal 100c being adapted to form a seal around a surgical instrument. The trocar seal 100c comprises a housing 10c having an axis 12c extending between a proximal end 14c and a distal end 16c and forming a working channel 18c sized and configured to receive the surgical instrument, and an elastomeric septum seal 20c having a proximal face and a distal face, the septum seal 20c being disposed in the housing 10c and extending transverse to the axis 12c of the housing across the working channel 18c. With this aspect, the seal 20c further includes an annular rib 28 incorporated onto the distal face of the seal 20c to prevent inversion as the surgical instrument is withdrawn from the trocar seal 100c. The annular rib 28 serves to reinforce the face of the septum seal 20c and thus prevents inversion. The annular rib 28 is configured so that side-to-side movement or floatation of the septum seal 20c is not compromised. The annular rib 28 may or may not be integral to the septum seal 20c. Alternatively, the annular rib 28 may be incorporated onto the proximal face of the septum seal 20c.

Figure 4:
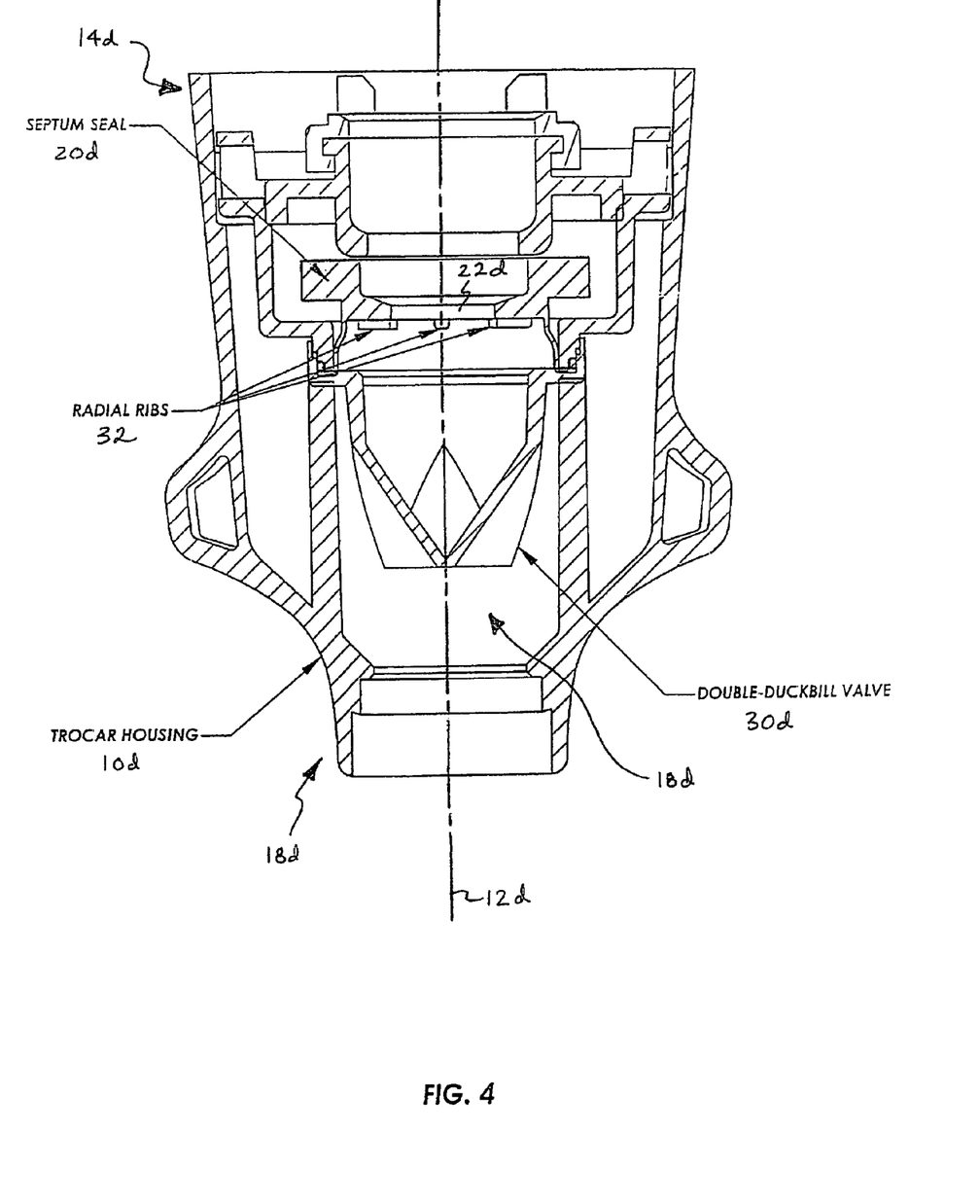
FIG. 4 illustrates an axial cross-section view of a trocar seal including a septum seal and a plurality of radial ribs in accordance to a fourth embodiment of the invention.

Referring to FIG. 4, there is shown an axial cross-section view of a trocar seal 100d, wherein elements of structures similar to those previously discussed are designated by the same reference numeral followed by the lower case letter "d", that is adapted to form a seal around a surgical instrument. The trocar seal 100d comprises a housing 10d having an axis 12d extending between a proximal end 14d and a distal end 16d and forming a working channel 18d sized and configured to receive the surgical instrument, and an elastomeric septum seal 20d having a proximal face and a distal face, the septum seal 20d being disposed in the housing 10d and extending transverse to the axis 12d of the housing across the working channel 18d. In this aspect, the seal 20d further includes a plurality of radially extending ribs 32 incorporated onto the distal face of the seal 20d to prevent inversion as the surgical instrument is withdrawn from the trocar seal 100d. The radially extending ribs 32 serve to reinforce the face of the septum seal 20d and thus prevent inversion. The ribs 32 are configured so that side-to-side movement or floatation of the septum seal 20d is not compromised. The radially extending ribs 32 may or may not be integral to the septum seal 20d. Alternatively, the radially extending ribs 32 may be incorporated onto the proximal face of the septum seal 20d.

Figure 5:
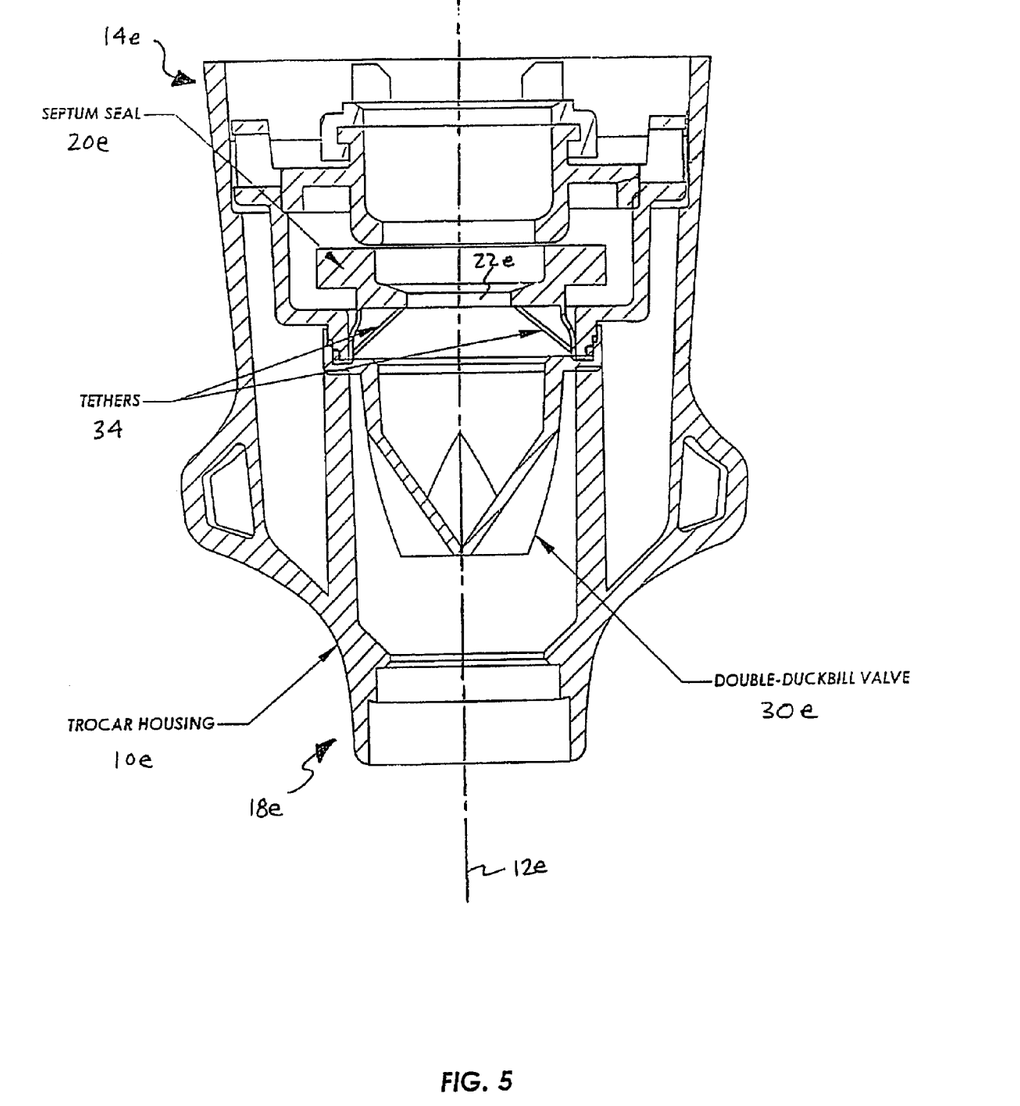
FIG. 5 illustrates an axial cross-section view of a trocar seal including a septum seal and a plurality of tethers in accordance to a fifth embodiment of the invention.

In yet another aspect of the invention as illustrated in FIG. 5, there is shown an axial cross-section view of a trocar seal 100e, wherein elements of structures similar to those previously discussed are designated by the same reference numeral followed by the lower case letter "e", that is adapted to form a seal around a surgical instrument. The trocar seal 100e comprises a housing 10e having an axis 12e extending between a proximal end 14e and a distal end 16e and forming a working channel 18e sized and configured to receive the surgical instrument, and an elastomeric septum seal 20e having a proximal face and a distal face, the septum seal 20e being disposed in the housing 10e and extending transverse to the axis 12e of the housing across the working channel 18e. In this aspect, the seal 20e further includes a plurality of tensile elements or tethers 34 incorporated onto the distal face of the seal 20e to prevent inversion as the surgical instrument is withdrawn from the trocar seal 100e. The tensile elements 34 serve to reinforce the face of the septum seal 20e and thus prevent inversion. The tensile elements 34 may be configured from surgical suture and may be integral to the septum seal 20e. In another aspect, the septum seal 20e may further comprise a sidewall including the tensile elements 34 extending from the sidewall to the distal face of the septum seal 20e and serving to tether the distal face of the seal downward and thus preventing inversion.

The invention further contemplates any structure, whether or not it is attached to the septum valve, which will inhibit movement of the valve in the proximal direction upon withdrawal of an instrument. This might include any structure disposed on the distal side of the septum valve which would be placed in tension if the valve tended to move proximally. It would also include any structure disposed on the proximal side of the valve which would typically be placed in compression if the valve were to move in the proximal direction.

It will be understood that many other modifications can be made to the various disclosed embodiments without departing from the spirit and scope of the invention. For these reasons, the above description should not be construed as limiting the invention, but should be interpreted as merely exemplary of preferred embodiments.

The invention claimed is:

1. A trocar seal adapted to form a seal around a surgical instrument, comprising:
   a housing having an axis extending between a proximal end and a distal end and forming a working channel sized and configured to receive the surgical instrument;
   an elastomeric septum seal having a proximal face and a distal face, the septum seal being disposed in the housing and extending transverse to the axis of the housing across the working channel;
   portions of the septum seal defining a hole having a diameter less than or equal to the diameter of the surgical instrument so that during insertion of the instrument along the working channel the septum seal forms a seal with the instrument; and
   at least one structure formed integrally with or proximate to the septum seal to prevent inversion of the septum seal upon withdrawal of the surgical instrument;
   wherein the structure is integrally formed on the proximal face of the septum seal to reinforce the seal.

2. A trocar seal adapted to form a seal around a surgical instrument, comprising:
   a housing having an axis extending between a proximal end and a distal end and forming a working channel sized and configured to receive the surgical instrument;
   an elastomeric septum seal having a proximal face and a distal face, the septum seal being disposed in the housing and extending transverse to the axis of the housing across the working channel;
   portions of the septum seal defining a hole having a diameter less than or equal to the diameter of the surgical instrument so that during insertion of the instrument along the working channel the septum seal forms a seal with the instrument; and
   at least one structure formed integrally with or proximate to the septum seal to prevent inversion of the septum seal upon withdrawal of the surgical instrument;
   wherein the structure is integrally formed on the distal face of the septum seal to tether the distal face of the seal downward.

3. The trocar seal of claim 2, wherein the structure is an annular reinforcement.

4. The trocar seal of claim 3, wherein the annular reinforcement is formed so as not to prevent side-to-side movement or floatation of the seal.

5. The trocar seal of claim 1, wherein the structure is an annular reinforcement.

6. The trocar seal of claim 2, wherein the structure is an annular rib.

7. The trocar seal of claim 6, wherein the annular rib is formed so as not to prevent floatation of the seal.

8. The trocar seal of claim 1, wherein the structure is an annular rib.

9. The trocar seal of claim 3, further comprising a plurality of radially extending ribs formed on the distal face of the septum seal to reinforce the seal.

10. The trocar seal of claim 9, wherein the plurality of radially extending ribs are formed so as not to prevent floatation of the seal.

11. The trocar seal of claim 1, further comprising a plurality of radially extending ribs formed on the proximal face of the septum seal to reinforce the seal.

12. The trocar seal of claim 2, further comprising a tensile element formed on the distal face of the septum seal.

13. The trocar seal of claim 12, wherein the tensile element is formed from surgical suture, an elastomer, a thermoplastic, or a metal wire.

14. A trocar seal adapted to form a seal around a surgical instrument, comprising:
   a housing having an axis extending between a proximal end and a distal end and forming a working channel sized and configured to receive the surgical instrument;
   an elastomeric septum seal having a proximal face and a distal face, the septum seal being disposed in the housing and extending transverse to the axis of the housing across the working channel;
   portions of the septum seal defining a hole having a diameter less than or equal to the diameter of the surgical instrument so that during insertion of the instrument along the working channel the septum seal forms a seal with the instrument; and
   at least one structure formed integrally with or proximate to the septum seal to prevent inversion of the septum seal upon withdrawal of the surgical instrument;
   wherein the structure includes any structure disposed distally of the septum seal and is placed in tension when the seal is moved proximally.

15. A trocar seal adapted to form a seal around a surgical instrument, comprising:
   a housing having an axis extending between a proximal end and a distal end and forming a working channel sized and configured to receive the surgical instrument;
   an elastomeric septum seal having a proximal face and a distal face, the septum seal being disposed in the housing and extending transverse to the axis of the housing across the working channel;
   portions of the septum seal defining a hole having a diameter less than or equal to the diameter of the surgical instrument so that during insertion of the instrument along the working channel the septum seal forms a seal with the instrument; and
   at least one structure formed integrally with or proximate to the septum seal to prevent inversion of the septum seal upon withdrawal of the surgical instrument;
   wherein the structure includes any structure disposed proximally of the septum seal and is placed in compression when the seal is moved proximally.

16. A trocar adapted to form a seal around a surgical instrument, comprising:
   a cannula having an axis extending between a proximal end and a distal end;
   a housing disposed at the proximal of the cannula and forming with the cannula a working channel sized and configured to receive the surgical instrument;
   an elastomeric septum seal having a proximal face and a distal face, the septum seal being disposed in the housing and extending transverse to the axis of the cannula across the working channel;
   portions of the septum seal defining a hole having a diameter less than or equal to the diameter of the surgical instrument so that during insertion of the instrument along the working channel the septum seal forms a seal with the instrument; and
   at least one structure formed integrally with or proximate to the septum seal to prevent inversion of the septum seal upon withdrawal of the surgical instrument;
   wherein the structure is integrally formed on the proximal face of the septum seal to reinforce the seal.

17. A trocar adapted to form a seal around a surgical instrument, comprising:
   a cannula having an axis extending between a proximal end and a distal end;
   a housing disposed at the proximal of the cannula and forming with the cannula a working channel sized and configured to receive the surgical instrument;
   an elastomeric septum seal having a proximal face and a distal face, the septum seal being disposed in the housing and extending transverse to the axis of the cannula across the working channel;
   portions of the septum seal defining a hole having a diameter less than or equal to the diameter of the surgical instrument so that during insertion of the instrument along the working channel the septum seal forms a seal with the instrument; and
   at least one structure formed integrally with or proximate to the septum seal to prevent inversion of the septum seal upon withdrawal of the surgical instrument;
   wherein the structure is integrally formed on the distal face of the septum seal to tether the distal face of the seal downward.

18. The trocar of claim 17, wherein the structure is an annular reinforcement.

19. The trocar of claim 18, wherein the annular reinforcement is formed so as not to prevent side-to-side movement or floatation of the seal.

20. The trocar of claim 16, wherein the structure is an annular reinforcement.

21. The trocar of claim 17, wherein the structure is an annular rib.

22. The trocar of claim 21, wherein the annular rib is formed so as not to prevent side-to-side movement or floatation of the seal.

23. The trocar of claim 16, wherein the structure is an annular rib.

24. The trocar of claim 17, further comprising a plurality of radially extending ribs formed on the distal face of the septum seal to reinforce the seal.

25. The trocar of claim 24, wherein the plurality of radially extending ribs are formed so as not to prevent side-to-side movement or floatation of the seal.

26. The trocar of claim 16, further comprising a plurality of radially extending ribs formed on the proximal face of the septum seal to reinforce the seal.

27. The trocar of claim 17, further comprising a tensile element formed on the distal face of the septum seal.

28. The trocar of claim 27, wherein the tensile element is formed from surgical suture, an elastomer, a thermoplastic, or a metal wire.

29. A trocar adapted to form a seal around a surgical instrument, comprising:
   a cannula having an axis extending between a proximal end and a distal end;
   a housing disposed at the proximal of the cannula and forming with the cannula a working channel sized and configured to receive the surgical instrument;
   an elastomeric septum seal having a proximal face and a distal face, the septum seal being disposed in the housing and extending transverse to the axis of the cannula across the working channel;

portions of the septum seal defining a hole having a diameter less than or equal to the diameter of the surgical instrument so that during insertion of the instrument along the working channel the septum seal forms a seal with the instrument; and at least one structure formed integrally with or proximate to the septum seal to prevent inversion of the septum seal upon withdrawal of the surgical instrument;

wherein the structure includes any structure disposed distally of the septum seal and is placed in tension when the seal is moved proximally.

30. A trocar adapted to form a seal around a surgical instrument, comprising:

a cannula having an axis extending between a proximal end and a distal end;

a housing disposed at the proximal of the cannula and forming with the cannula a working channel sized and configured to receive the surgical instrument;

an elastomeric septum seal having a proximal face and a distal face, the septum seal being disposed in the housing and extending transverse to the axis of the cannula across the working channel;

portions of the septum seal defining a hole having a diameter less than or equal to the diameter of the surgical instrument so that during insertion of the instrument along the working channel the septum seal forms a seal with the instrument; and at least one structure formed integrally with or proximate to the septum seal to prevent inversion of the septum seal upon withdrawal of the surgical instrument;

wherein the structure includes any structure disposed proximally of the septum seal and is placed in compression when the seal is moved proximally.

* * * * *